United States Patent [19]

Zurflüh

[11] 4,162,328

[45] Jul. 24, 1979

[54] CYCLOPROPANE CARBOXYLIC ACID ESTERS

[75] Inventor: René Zurflüh, Bülach, Switzerland

[73] Assignee: Hoffmann-La Roche Inc., Nutley, N.J.

[21] Appl. No.: 889,598

[22] Filed: Mar. 23, 1978

[30] Foreign Application Priority Data

Apr. 1, 1977 [au] Austria ............................. 2308/77

[51] Int. Cl.$^2$ .................... C07C 69/74; A01N 9/24
[52] U.S. Cl. ..................................... 424/305; 560/124
[58] Field of Search ......................... 560/124; 424/305

[56] References Cited

U.S. PATENT DOCUMENTS

| | | | |
|---|---|---|---|
| 3,567,740 | 3/1971 | Matsui | 560/124 |
| 3,761,506 | 9/1973 | Osbond | 560/124 |
| 3,813,427 | 5/1974 | Osbond | 560/124 |
| 3,849,466 | 11/1974 | Henrick | 560/124 |
| 3,860,625 | 1/1975 | Henrick | 560/124 |
| 3,876,682 | 4/1975 | Henrick | 560/124 |
| 3,903,128 | 9/1975 | Henrick | 260/455 R |
| 3,925,460 | 12/1975 | Henrick | 560/124 |
| 3,957,849 | 5/1976 | Henrick | 560/124 |

FOREIGN PATENT DOCUMENTS 45-7073  3/1970  Japan ..................................... 560/124

OTHER PUBLICATIONS

Henrick, J. Agric. Food Chemi, v. 24, pp. 1023-1029 (1976).
Chem. Abst., 72:110625(b) (1970).

Primary Examiner—James O. Thomas, Jr.
Assistant Examiner—Michael Shippen
Attorney, Agent, or Firm—Jon S. Saxe; Bernard S. Leon; George W. Johnston

[57] ABSTRACT

Cyclopropane carboxylic acid esters useful as pesticides and methods for their manufacture are disclosed.

21 Claims, No Drawings

CYCLOPROPANE CARBOXYLIC ACID ESTERS

SUMMARY OF THE INVENTION

The present invention discloses cyclopropane carboxylic acid esters of the following formula:

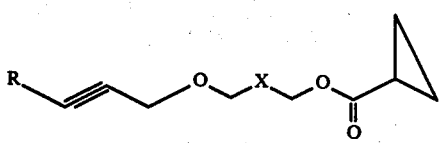
I wherein X is alkylene having 6 to 10 carbon atoms, 1,4-cyclohexylene or 1,4-phenylene; and R is hydrogen or alkyl having 1 to 3 carbon atoms.

The compounds of formula I are useful as pesticides and are especially suitable for the control of insects and mites, particularly spider mites.

DETAILED DESCRIPTION OF THE INVENTION

The cyclopropane carboxylic acid esters of the present invention have the following formula

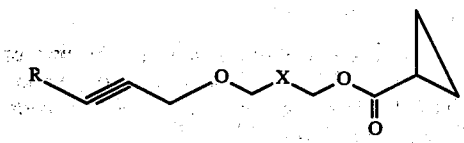
I wherein X is alkylene having 6 to 10 carbon atoms, 1,4-cyclohexylene or 1,4-phenylene; and R is hydrogen or alkyl having 1 to 3 carbon atoms.

As used herein, alkylene can be straight-chain or branched-chain alkylene having 6-10 carbon atoms. Halogen includes fluorine, chlorine, bromine and iodine. Alkali metals include lithium, sodium, potassium, rubidium and cesium. Alkaline earth metals include beryllium, magnesium, calcium and strontium.

Cyclopropane carboxylic acid esters of formula I wherein R is hydrogen and X is a straight-chain alkylene group containing 8 to 10 carbon atoms or 1,4-cyclohexylene are preferred.

Especially preferred cyclopropane carboxylic acid esters of formula I are:
  cyclopropane carboxylic acid 10-(2-propynyloxy)decyl ester;
  cyclopropane carboxylic acid 11-(2-propynyloxy)undecyl ester;
  cyclopropane carboxylic acid 12-(2-propynyloxy)dodecyl ester; and
  cyclopropane carboxylic acid {4-[(2-propynyloxy)methyl]-cyclohexyl}methyl ester.

According to the present invention, the cyclopropane carboxylic acid esters of formula I may be manufactured by the following procedures:

Embodiment A: reacting an ester of the formula:

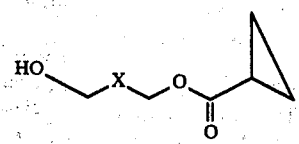
II wherein X is as defined previously with a compound of the formula:

III wherein R is as defined above and Z is chlorine, bromine, iodine, mesyloxy or tosyloxy in the presence of an alcoholate-forming agent; or Embodiment B: reacting an alcohol of the formula:

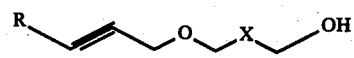
IV wherein R and X are as defined previously with cyclopropane carboxylic acid or a reactive derivative thereof; or Embodiment C: reacting an ester of the formula:

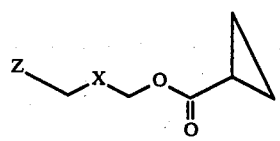
V wherein X and Z are as defined above with an alcohol of the general formula

VI wherein R is as defined previously in the presence of an alcoholate-forming agent.

The reaction of an ester of formula II with a compound of formula III in accordance with Embodiment A of the present process is carried out in an inert organic solvent, preferably dimethylformamide, dioxane, hexamethylphosphoric acid triamide, tetrahydrofuran or dimethoxyethane or a mixture of two or more of these solvents. A corresponding alcohol is conveniently used and the reaction is carried out in the presence of an alkali metal or alkaline earth metal, a corresponding hydride or amide or an alkali metal hydroxide. In this case, the corresponding alcoholate is formed from the alcohol. Preferred alkali metals are sodium and potassium and preferred alkaline earth metals are calcium and magnesium. The temperature at which the reaction is carried out is not critical. Conveniently, the reaction can be carried out at a temperature between 0°–20° C. and the boiling point of the reaction mixture. The reaction is preferably carried out at a temperature of 50° C. to 70° C., especially when a compound of formula III wherein Z is bromine is used as the starting material.

In accordance with Embodiment B of the present process, cyclopropane carboxylic acid or a reactive derivative thereof is reacted with an alcohol of formula IV or with a reactive derivative thereof. The reactive derivative of cyclopropane carboxylic acid is an acid halide, an acid anhydride, an imidazolide, an ester formed with a low-boiling alcohol, an alkali metal salt, a silver salt or a salt of a tertiary amine. Halides or sulphonic acid esters are examples of reactive derivatives of an alcohol of formula IV.

The reaction of an alcohol of formula IV with cyclopropane carboxylic acid is preferably carried out in a suitable inert solvent at room temperature or at an elevated temperature and by using procedures which are suitable for the splitting off of water. For example, suitable procedures include carrying out the reaction in the presence of dicyclohexylcarbodiimide or azeotropically distilling off the water formed from the catalyzed reaction mixture. When a cyclopropane carboxylic acid halide is used as the starting material, the reaction thereof with an alcohol of formula IV is carried out at room temperature and in the presence of an acid acceptor such as a base. Among the preferred bases are organic bases such as tertiary amines (e.g., pyridine or triethylamine). Among the preferred inorganic bases are alkali metal hydroxide and alkaline earth metal hydroxides. A particularly preferred inorganic base is sodium hydroxide. The corresponding cyclopropane carboxylic acid ester of formula I is obtained in a high yield. Cyclopropane carboxylic acid chloride is the preferred cyclopropane carboxylic acid halide. The reaction is preferably carried out in the presence of an inert solvent such as benzene, toluene or petroleum ether.

The compounds of formula I can be manufactured in a good yield by reacting the imidazolide of cyclopropane carboxylic acid with an alkali metal alcoholate derived from an alcohol of formula IV or with an alcohol of formula IV together with a catalytic amount of an alkali metal alcoholate. The reaction is preferably carried out in an inert solvent such as tetrahydrofuran or dimethoxyethane and at room temperature.

When cyclopropane carboxylic acid anhydride is used as the starting material in Embodiment B of the present process, the cyclopropane carboxylic acid esters of formula I can be manufactured by reacting this acid anhydride with an alcohol of formula IV at room temperature (preferably at an elevated temperature) and in the presence of a solvent such as toluene or xylene. If a halide or sulfonic acid ester of an alcohol of formula IV is used, the cyclopropane carboxylic acid is generally utilized in the form of an alkali metal salt, a silver salt or a salt formed with a tertiary amine. The salt can be prepared in situ by adding the corresponding base to cyclopropane carboxylic acid. In this case, a solvent such as benzene, acetone, methyl ethyl ketone or dimethylformamide is preferably used and the reaction is preferably carried out while the reaction mixture is heated to the boiling point or below the boiling point of the selected solvent. The preferred halides of the alcohols of formula IV are chloride and bromide.

The reaction of an ester of formula V with an alcohol of formula VI in accordance with Embodiment C of the present process is carried out under the same conditions as described hereinbefore in connection with Embodiment A of the present process.

It is understood that formula I also includes geometric isomers. For example, in accordance with the present invention the 1,4-cyclohexylene ring occurs in two geometric configurations.

The ester starting materials of formula II are prepared from the corresponding diols under the same conditions as described hereinbefore in connection with Embodiment B of the present process.

The alcohol starting materials of formula IV are prepared under the same conditions as described hereinbefore in connection with Embodiment A of the present process.

The ester starting materials of formula V can be prepared, for example, by reacting an alcohol of the formula:

wherein X and Z are as defined above with cyclopropane carboxylic acid or a reactive derivative thereof under the same conditions as described earlier in connection with Embodiment B of the present process.

Moreover, ester starting materials of the formula:

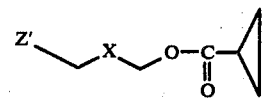

wherein X is as defined previously and Z' is mesyloxy or tosyloxy can be prepared by reacting an ester of formula II with methanesulfonyl chloride or p-toluenesulfonyl chloride in the presence of an acid acceptor.

The ester starting materials of formula II can also be prepared, for example, by reacting a halohydrin of the general formula:

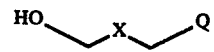

wherein X is as defined above and Q is chlorine or bromine with cyclopropane carboxylic acid in the manner previously described in connection with Embodiment B of the present process.

The present invention is also concerned with pesticidal compositions which contain an essential active ingredient or essential active ingredients one or more of the cyclopropane carboxylic acid esters of formula I in association with a compatible carrier material. The pesticidal compositions conveniently contain at least one of the following materials: carrier substances, wetting agents, inert diluents and solvents.

Further, the present invention is concerned with a method of rendering a locus subject to or subjected to attack by pests free from such attack. This method comprises applying to the locus the hereinbefore described pesticidal composition. Illustratively, the locus can be plants, animals, soil, objects and surfaces.

The compounds of formula I are accordingly quite generally of value as pesticides, especially as acaricides and insecticides. In particular, the compounds of formula I are effective against mites, ticks, white flies, green flies, caterpillars and beetles, with the ovicidal activity being particularly important. Additionally, the cyclopropane carboxylic acid esters of formula I also have systemic activity.

The cyclopropane carboxylic acid esters of formula I are, inter alia, active against spider mites of the family Tetranychidae such as *Tetranychus urticae, Tetranychus canadensis, Tetranychus cinnabarinus, Tetranychus pacificus, Bryobia praetiosa, Oligonychus pratensis, Oligonychus ilicis, Panonychus citri, Panonychus ulmi* and related species. Moreover, they are active against members of the family Tarsonemidae such as *Steneotarsonemus pallidus*, or of the sub-group Eriophyidae such as *Phyllocoptruta oleivora*.

Furthermore, the cyclopropane carboxylic acid esters of formula I are especially active against white flies of the sub-group Aleurodoidae such as *Bemisia tabaci, Bemisia citricola, Aleurodes proletella, Aleurocanthus*

*spiniferus, Aleurocanthus woglumi, Aleurolobus marlatti, Aleurothrixus floccosus, Dialeurodes citri, Trialeurodes vaporariorum* and related species.

The acaricidal activity of the compounds of formula I represents a preferred aspect of the present invention. For example, cyclopropane carboxylic acid 10-(2-propynyloxy)decyl ester has an activity of 100% in a concentration of $10^{-7}$ g/cm$^2$ in tests against spider mite eggs. The activity against white flies represents a further preferred aspect of the present invention. For example, cyclopropane carboxylic acid 12-(2-propynyloxy)dodecyl ester in a concentration of 0.03% by volume has an activity of 100% against white fly eggs and an activity of 99% against white fly larvae.

The cyclopropane compounds of formula I are, in general, insoluble in water and can be made into a ready-to-use form according to any method which is customarily used for the formulation of water-insoluble compounds.

If desired, the cyclopropane carboxylic acid esters of formula I can be dissolved in a water-immiscible solvent (e.g., a high-boiling hydrocarbon) which conveniently contains dissolved emulsifiers, so that it acts as a self-emulsifiable oil upon addition to water.

The compounds of formula I can also be mixed with a wetting agent, with or without an inert diluent, to form a wettable powder which is soluble or dispersible in water. Alternatively, they can be mixed with inert diluents to form a solid or pulverous product.

Inert diluents with which the cyclopropane carboxylic acid esters of formula I can be processed are solid inert media, including pulverous or finely divided solid materials illustratively including clays, sands, talc, mica, fertilizers and the like. The resulting composition can be in the form of dusts or as materials having a larger particle size.

Illustratively, the wetting agents can be anionic compounds such as soaps, fatty sulfate esters (e.g., dodecyl sodium sulfate, octadecyl sodium sulfate and cetyl sodium sulfate), fatty-aromatic sulfonates (e.g., alkylbenzene sulfonates and butylnaphthalene sulfonates) and complex fatty sulfonates (e.g., amide condensation products of oleic acid and N-methyltaurin or sodium sulfonate of dioctyl succinate).

The wetting agents can also be non-ionic wetting agents such as, for example, condensation products of fatty acids, fatty alcohols or fat-substituted phenols with ethylene oxide, or fatty acid esters and ethers of sugars or polyvalent alcohols or the products which are obtained from the latter by condensation with ethylene oxide, or the products which are known as block copolymers of ethylene oxide and propylene oxide.

The wetting agents can also be cationic agents such as, for example, cetyltrimethylammonium bromide and the like.

The pesticidal compositions provided by the present invention can also be present in the form of an aerosol having a propellant gas (e.g., a polyhalogenated alkane such as dichlorodifluoromethane), a co-solvent and a wetting agent.

The pesticidal compositions provided by the present invention can contain, in addition to one or more of the cyclopropane carboxylic acid esters of formula I, synergists and other active insecticides, insect growth regulators, bactericides and fungicides.

In their various fields of application, the cyclopropane carboxylic acid esters of formula I can be used in different ratios. For example, for the treatment of plants to control pests thereon, the present cyclopropane carboxylic acid esters can be conveniently used in an amount of about 100–2000 g/hectare. For the treatment of animals to control ectoparasites thereon, the animal is conveniently dipped in a solution containing 100–1000 ppm of a compound of formula I or sprayed with such a solution. Because the cyclopropane carboxylic acid esters of the present invention have an acute toxicity of about 1000 mg/kg., they are only very slightly toxic to vertebrates.

The following non-limiting examples illustrate the present invention. The ether utilized is diethyl ether.

EXAMPLE 1

39.3 g. of a 55% sodium hydride suspension in oil are washed twice with hexane to remove the oil and are covered with 100 ml. of absolute tetrahydrofuran. While stirring, there is added dropwise at room temperature a solution of 209 g. of 1,10-decanediol in 600 ml. of absolute tetrahydrofuran and 360 ml. of absolute dimethylformamide. Subsequently, 85 ml. of hexamethylphosphoric acid triamide are added and the resulting mixture is stirred at 75° C. for 18 hours. Then, 110 g. of propargyl bromide are added thereto and the mixture is stirred at 75° C. for 6 hours. The cooled mixture is filtered; the residue is washed with ether and the filtrate and washings are concentrated on a rotary evaporator. The concentrated mixture is poured onto ice-water, exhaustively extracted with ether and the extract is washed with water and saturated sodium chloride solution, dried over sodium sulfate and evaporated. By chromatography on silica gel with hexane/ethyl acetate (60:40 parts by volume) there is obtained pure 10-(2-propynyloxy)-1-decanol; $n_D^{24} = 1.4590$.

In an analogous manner, from 1,12-decanediol there is obtained 12-(2-propynyloxy)-1-dodecanol; boiling point 114°–115° C./0.002 mmHg; melting point 35°–35.5° C.

EXAMPLE 2

91 g. of 10-(2-propynyloxy)-1-decanol are dissolved in 500 ml. of ether and treated with 37 g. of pyridine. While cooling with ice and stirring, there are added dropwise 49.5 g. of cyclopropane carboxylic acid chloride and 50 ml. of ether thereto. Subsequently, the mixture is stirred at room temperature for 3 hours. The mixture is poured onto ice-water, exhaustively extracted with ether and the extract is washed with 2 N hydrochloric acid, water, 10% potassium bicarbonate solution, semi-saturated and saturated sodium chloride solution, dried over sodium sulfate and evaporated. By chromatography on silica gel with hexane/ethyl acetate (95:5 parts by volume) there is obtained pure cyclopropane carboxylic acid 10-(2-propynyloxy)decyl ester; $n_D^{25} = 1.4616$.

In an analogous manner, from 12-(2-propynyloxy)-1-dodecanol there is obtained cyclopropane carboxylic acid 12-(2-propynyloxy)dodecyl ester; boiling point (bulb-tube) 150° C./0.035 mmHg; $n_D^{22} = 1.4627$.

EXAMPLE 3

In an analogous manner to that described in Example 1, from 1,4-bis(hydroxymethyl)-cyclohexane there is obtained 4-[(2-propynyloxy)methyl]-1-cyclohexanemethanol having a boiling point (bulb-tube) of 145° C./0.03 mmHg. Therefrom there is obtained, by reaction with cyclopropane carboxylic acid chloride in a manner analogous to that described in Example 2, cyclopropane carboxylic acid {4-[(2-propynyloxy)methyl] cyclohexyl} methyl ester of boiling point (bulb-tube) 150° C./0.02 mmHg.

EXAMPLE 4

In an analogous manner to that described in Example 1, from 4-(hydroxymethyl)benzyl alcohol and propargyl bromide there is obtained 4-[(2-propynyloxy)methyl]benzyl alcohol. This alcohol is reacted in an analogous manner to that described in Example 2 with cyclopropane carboxylic acid chloride to give cyclopropane carboxylic acid p-[(2-propynyloxy)methyl]benzyl ester.

EXAMPLE 5

3.7 g. of a 55% sodium hydride suspension in oil are washed with hexane to remove the oil and are covered with 100 ml. of dimethylformamide. While stirring, there are slowly added dropwise 4.71 g. of propargyl alcohol dissolved in 100 ml. of dimethylformamide. The temperature is raised to 40° C. and the reaction is allowed to proceed for 4 hours. The resulting mixture is cooled in an ice-bath and is treated dropwise with a solution of 22.35 g. of cyclopropane carboxylic acid 11-bromoundecyl ester in 70 ml. of dimethylformamide. After stirring at room temperature for 2 hours, the mixture is poured onto 500 ml. of ice-water, extracted with ether and the ether extract is washed with a semi-saturated and saturated sodium chloride solution, dried over sodium sulfate and evaporated. By chromatography on silica gel there is obtained pure cyclopropane carboxylic acid 11-(2-propynyloxy)undecyl ester; $n_D^{20} = 1.4632$.

The cyclopropane carboxylic acid 11-bromoundecyl ester used as the starting material in this Example is prepared from 11-bromoundecanol and cyclopropane carboxylic acid chloride in an analogous manner to that described in Example 2.

EXAMPLE 6

In an analogous manner to that described in Example 2, from 12-bromododecan-1-ol and cyclopropane carboxylic acid chloride there is obtained cyclopropane carboxylic acid 12-bromododecyl ester of melting point 29°–31° C.

EXAMPLE 7

In an analogous manner to that described in Example 5, from 2-butyn-1-ol and cyclopropane carboxylic acid 12-bromododecyl ester there is obtained cyclopropane carboxylic acid 12-(2-butynyloxy)dodecyl ester of melting point 38°–40° C.

EXAMPLE 8

The cyclopropane carboxylic acid esters of formula I can be formulated as follows:

| | g/l |
|---|---|
| Cyclopropane carboxylic acid ester of formula I | 500.0 |
| Mixture of castor oil and ethyleneoxy condensation products with ca 25 mol of ethylene oxide in the ratio 3:1 | 100.0 |
| Epoxidized soya oil with an oxirane oxygen content of 6% by | 25.0 |
| Butylated hydroxytoluene | 10.0 |
| Solvent consisting of a mixture of mono-, di- and tri(lower alkyl)benzenes ad | 1000 ml. |

The following biological experiments demonstrate the efficacy of the cyclopropane carboxylic acid esters of the present invention.

EXAMPLE 9

Bean leaf roundels (3.8 cm²) are infected with 20–30 spider mites in the mobile stage. Subsequently, the roundels are sprayed with an acetonic solution which contains the compound to be tested in known concentrations. The treated roundels are incubated at 25° C. and at 60% relative atmospheric humidity. Untreated roundels and roundels treated with acetone are used as the controls. After 6 days, the results are given in percentage (%) of reduction of the mobile stages in comparison to the controls. The results are compiled in the following Table.

Table 1

| Cyclopropane carboxylic acid ester | Concentration $10^{-x}$ g/cm² | % Reduction of the mobile stages |
|---|---|---|
| Cyclopropane carboxylic acid 10-(2-propynyloxy)-decyl ester | 5 | 100 |
| Cyclopropane carboxylic acid 12-(2-propynyloxy) dodecyl ester | 5 | 100 |
| Cyclopropane carboxylic acid [4-[(2-propynyloxy)methyl]-cyclohexyl]methyl ester | 5 | 100 |
| Cyclopropane carboxylic acid [(2-propynyloxy)methyl]benzyl ester | 5 | 97 |

EXAMPLE 10

In a field experiment against *Tetranychus urticae*, vines (Gamay and Chasselas) were treated with cyclopropane carboxylic acid 12-(2-propynyloxy)dodecyl ester. The ester was used in the form of an emulsifiable concentrate formulated in accordance with Example 8. The concentration of ester was 0.075% by volume and the amount sprayed was 2500 liters per hectare. The experiment embraced 3 plots per variant and each plot measured 13 m². Untreated plots are used as the controls.

The number of mobile spider mite stages on each of 10 vine leaves per plot were counted and the percentage reduction in comparison to the untreated controls was calculated. The results are compiled in the following Table.

Table 2

| | | % Reduction (days after the treatment) | |
|---|---|---|---|
| | % | 11 | 42 |
| Dicofol* | 0.05** | 62 | 84 |
| Cyclopropane carboxylic acid 12-(2-propynyloxy)-dodecyl ester | 0.075 | 97 | 100 |

* = 2,2,2-trichloro-1,1-bis(4-chlorophenyl)ethanol
** = Concentration recommended for use

EXAMPLE 11

In a field experiment against *Phyllocoptruta oleivora* in Florida, U.S.A., orange trees were treated with cyclopropane carboxylic acid 10-(2-propynyloxy)decyl ester. The ester was used in the form of an emulsifiable concentrate formulated in accordance with Example 8. The ester was used in a concentration of 0.025% by volume and the treatment was carried out until the spray liquor began to drop off the trees. The experiment embraced 2 plots per variant each with one orange tree. Untreated plots are used as the controls.

The number of mites on each of 10 leaves per plot was counted and the percentage reduction in comparison to the untreated controls was calculated. The results are compiled in the following Table.

Table 3

|  | % | % Reduction (days after the treatment) | | |
|---|---|---|---|---|
|  |  | 7 | 14 | 21 |
| Chlorobenzilate* | 0.03** | 89 | 75 | 3 |
| Cyclopropane carboxylic acid 10-(2-propynyl-oxy)decyl ester | 0.025 | 97 | 94 | 91 |

\* = 4,4'-dichlorobenzilic acid ethyl ester
\*\* = concentration recommended for use

I claim:
1. A compound of the formula:

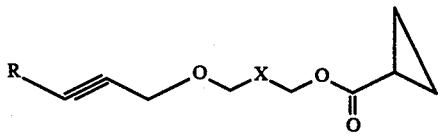

wherein X is alkylene having 6 to 10 carbon atoms, 1,4-cyclohexylene or 1,4-phenylene; and R is hydrogen or alkyl having 1 to 3 carbon atoms.
2. The compound of claim 1 wherein R is hydrogen and X is straight-chain alkylene having 6 to 10 carbon atoms or 1,4-cyclohexylene.
3. The compound of claim 1, cyclopropane carboxylic acid 10-(2-propynyloxy)decyl ester.
4. The compound of claim 1, cyclopropane carboxylic acid 12-(2-propynyloxy)dodecyl ester.
5. The compound of claim 1, cyclopropane carboxylic acid {4-[(2-propynyloxy)methyl]cyclohexyl} methyl ester.
6. The compound of claim 1, cyclopropane carboxylic acid 11-(2-propynyloxy)-undecyl ester.
7. The compound of claim 1, cyclopropane carboxylic acid p-[(2-propynyloxy)methyl]benzyl ester.
8. An insecticidal composition which comprises a compatible carrier material and as an active ingredient one or more compounds of the formula:

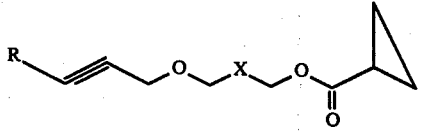

wherein X is alkylene having 6 to 10 carbon atoms, 1,4-cyclohexylene or 1,4-phenylene; and R is hydrogen or alkyl having 1 to 3 carbon atoms
in an amount which is effective as an insecticide.
9. An acaricidal composition which comprises a compatible carrier material and as an active ingredient one or more compounds of the formula:

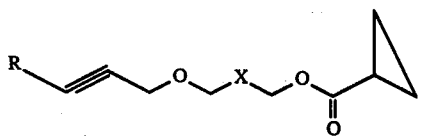

wherein X is alkylene having 6 to 10 carbon atoms, 1,4-cyclohexylene or 1,4-phenylene; and R is hydrogen or alkyl having 1 to 3 carbon atoms
in an amount which is effective as an acaricide.
10. The composition of claim 8 or 9 wherein the active ingredient is cyclopropane carboxylic acid 10-(2-propynyloxy)decyl ester.
11. The composition of claim 8 or 9 wherein the active ingredient is cyclopropane carboxylic acid 12-(2-propynyloxy)dodecyl ester.
12. The composition of claim 8 or 9 wherein the active ingredient is cyclopropane carboxylic acid {4-[(2-propynyloxy)methyl]cyclohexyl} methyl ester.
13. The composition of claim 8 or 9 wherein the active ingredient is cyclopropane carboxylic acid 11-(2-propynyloxy)undecyl ester.
14. The composition of claim 8 or 9 wherein the active ingredient is cyclopropane carboxylic acid p-[(2-propynyloxy)methyl]benzyl ester.
15. A method of rendering a locus subject to or subjected to attack by insects free from such attack, which method comprises applying to said locus an insecticidal composition having a compatible carrier material and as an active ingredient one or more compounds of the formula:

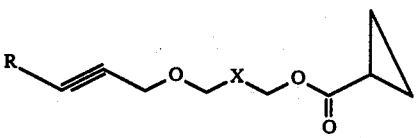

wherein X is alkylene having 6 to 10 carbon atoms, 1,4-cyclohexylene or 1,4-phenylene; and R is hydrogen or alkyl having 1 to 3 carbon atoms
in an amount which is effective as an insecticide.
16. A method of rendering a locus subject to or subjected to attack by acaricides free from such attack, which method comprises applying to said locus an acaricidal composition having a compatible carrier material and as an active ingredient one or more compounds of the formula:

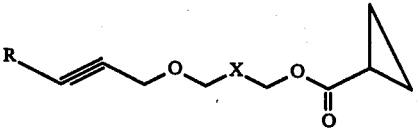

wherein X is alkylene having 6 to 10 carbon atoms, 1,4-cyclohexylene or 1,4-phenylene; and R is hydrogen or alkyl having 1 to 3 carbon atoms
in an amount which is effective as an acaricide.
17. The method of claim 15 or 16 wherein the active ingredient of the composition is cyclopropane carboxylic acid 10-(2-propynyloxy)decyl ester.
18. The method of claim 15 or 16 wherein the active ingredient of the composition is cyclopropane carboxylic acid 12-(2-propynyloxy)dodecyl ester.
19. The method of claim 15 or 16 wherein the active ingredient of the composition is cyclopropane carboxylic acid {4-[(2-propynyloxy)methyl]cyclohexyl}-methyl ester.
20. The method of claim 15 or 16 wherein the active ingredient of the composition is cyclopropane carboxylic acid 11-(2-propynyloxy)undecyl ester.
21. The method of claim 15 or 16 wherein the active ingredient of the composition is cyclopropane carboxylic acid p-[(2-propynyloxy)methyl]benzyl ester.

\* \* \* \* \*